(12) United States Patent
Cho et al.

(10) Patent No.: US 10,883,874 B2
(45) Date of Patent: Jan. 5, 2021

(54) DUAL COUPLER DEVICE, SPECTROMETER INCLUDING THE DUAL COUPLER DEVICE, AND NON-INVASIVE BIOMETRIC SENSOR INCLUDING THE SPECTROMETER

(71) Applicants: SAMSUNG ELECTRONICS CO., LTD., Suwon-si (KR); IMEC VZW, Leuven (BE)

(72) Inventors: Seongho Cho, Gwacheon-si (KR); Tom Claes, Merelbeke (BE); Dongho Kim, Seoul (KR)

(73) Assignees: SAMSUNG ELECTRONICS CO., LTD., Suwon-si (KR); IMEC VZW, Leuven (BE)

( * ) Notice: Subject to any disclaimer, the term of this patent is extended or adjusted under 35 U.S.C. 154(b) by 0 days.

(21) Appl. No.: 16/582,550

(22) Filed: Sep. 25, 2019

(65) Prior Publication Data

US 2020/0018646 A1 Jan. 16, 2020

Related U.S. Application Data

(63) Continuation of application No. 15/045,895, filed on Feb. 17, 2016, now Pat. No. 10,466,100.

(30) Foreign Application Priority Data

Feb. 17, 2015 (KR) .......................... 10-2015-0024020

(51) Int. Cl.
*G01J 3/02* (2006.01)
*G02B 6/124* (2006.01)
(Continued)

(52) U.S. Cl.
CPC .......... *G01J 3/0224* (2013.01); *A61B 5/0075* (2013.01); *A61B 5/1455* (2013.01);
(Continued)

(58) Field of Classification Search
CPC ...... G01J 3/0224; G01J 3/0205; G01J 3/0256; G01J 2003/1291; G01J 3/18;
(Continued)

(56) References Cited

U.S. PATENT DOCUMENTS 3,719,906 A 3/1973 Tournois
3,795,434 A 3/1974 Ash
(Continued)

FOREIGN PATENT DOCUMENTS

EP 0468612 A2 1/1992
EP 0647861 A1 4/1995
(Continued)

OTHER PUBLICATIONS

Communication dated Jul. 14, 2017 by the European Patent Office in counterpart European Patent Application No. 16 155 290.6.
(Continued)

*Primary Examiner* — Mohamed K Amara
(74) *Attorney, Agent, or Firm* — Sughrue Mion, PLLC (57) ABSTRACT

Provided are a dual coupler device configured to receive lights of different polarization components, a spectrometer including the dual coupler device, and a non-invasive biometric sensor including the spectrometer. The dual coupler device may include, for example, a first coupler layer configured to receive a light of a first polarization component among incident lights, and a second coupler layer configured to receive a light of a second polarization component among the incident lights, wherein a polarization direction of the light of the first polarization component is perpendicular to a polarization direction of the light of the second polarization component. The first coupler layer and the second coupler layer may be spaced apart from each
(Continued)

other and extended along a direction in which the light propagates in the first coupler layer and the second coupler layer.

20 Claims, 5 Drawing Sheets

(51) Int. Cl.

| | | |
|---|---|---|
| G01N 21/27 | (2006.01) | |
| G01J 3/18 | (2006.01) | |
| G01N 21/47 | (2006.01) | |
| A61B 5/145 | (2006.01) | |
| A61B 5/1455 | (2006.01) | |
| G01J 3/26 | (2006.01) | |
| G01J 3/36 | (2006.01) | |
| A61B 5/00 | (2006.01) | |
| G02B 6/10 | (2006.01) | |
| G02B 6/27 | (2006.01) | |
| G01J 3/12 | (2006.01) | |
| G02B 6/34 | (2006.01) | |

(52) U.S. Cl.
CPC .......... *A61B 5/14532* (2013.01); *G01J 3/021* (2013.01); *G01J 3/0205* (2013.01); *G01J 3/0256* (2013.01); *G01J 3/18* (2013.01); *G01J 3/1895* (2013.01); *G01J 3/26* (2013.01); *G01J 3/36* (2013.01); *G01N 21/27* (2013.01); *G01N 21/47* (2013.01); *G02B 6/124* (2013.01); *G01J 2003/1291* (2013.01); *G01N 2201/062* (2013.01); *G01N 2201/0612* (2013.01); *G01N 2201/0683* (2013.01); *G01N 2201/08* (2013.01); *G02B 6/105* (2013.01); *G02B 6/2726* (2013.01); *G02B 6/34* (2013.01)

(58) Field of Classification Search
CPC . A61B 5/0075; A61B 5/1455; A61B 5/14532; G02B 6/105; G02B 6/2726; G02B 6/124; G02B 6/34; G01N 2201/062; G01N 2201/0612; G01N 2201/0683; G01N 2201/08; G01N 21/27; G01N 21/47
See application file for complete search history.

(56) References Cited

U.S. PATENT DOCUMENTS

| | | | |
|---|---|---|---|
| 4,813,771 A | 3/1989 | Handschy et al. | |
| 5,220,573 A * | 6/1993 | Sakata | G02B 6/124 372/102 |
| 5,311,605 A | 5/1994 | Stewart | |
| 5,343,542 A * | 8/1994 | Kash | G02B 6/12007 372/45.01 |
| 5,784,507 A | 7/1998 | Holm-Kennedy et al. | |
| 5,915,051 A | 6/1999 | Damask et al. | |
| 6,151,429 A | 11/2000 | Kristensen et al. | |
| 6,373,868 B1 * | 4/2002 | Zhang | H01S 3/0941 372/19 |
| 6,690,873 B2 * | 2/2004 | Bendett | C03C 4/00 385/132 |
| 6,771,857 B1 * | 8/2004 | Domash | G02B 6/12007 349/201 |
| 6,801,310 B2 | 10/2004 | Kewitsch et al. | |
| 6,914,715 B2 | 7/2005 | Nakazawa et al. | |
| 6,944,369 B2 * | 9/2005 | Deliwala | B82Y 20/00 257/E27.112 |
| 6,963,118 B2 * | 11/2005 | Deliwala | B82Y 20/00 257/428 |
| 7,184,627 B1 * | 2/2007 | Gunn, III | G02B 6/12004 359/34 |
| 7,289,700 B1 | 10/2007 | Evans et al. | |
| 7,301,628 B2 * | 11/2007 | Cunningham | B01L 3/5085 356/326 |
| 7,324,267 B2 | 1/2008 | Melloni et al. | |
| 7,400,399 B2 | 7/2008 | Wawro et al. | |
| 7,454,103 B2 * | 11/2008 | Parriaux | G02B 5/1814 359/369 |
| 7,590,161 B1 | 9/2009 | Hug et al. | |
| 7,627,018 B1 | 12/2009 | Guilfoyle et al. | |
| 8,008,694 B2 | 8/2011 | Xu et al. | |
| 8,200,054 B1 * | 6/2012 | Li | G02B 6/34 385/37 |
| 8,493,562 B2 * | 7/2013 | Kopp | G02B 6/34 356/364 |
| 8,642,941 B2 * | 2/2014 | Vermeulen | G02B 6/4246 250/214 R |
| 9,410,891 B2 | 8/2016 | Fehr et al. | |
| 9,423,565 B2 | 8/2016 | Lealman et al. | |
| 9,435,961 B2 * | 9/2016 | Jiang | G02B 6/1223 |
| 9,651,718 B2 * | 5/2017 | Chen | G02B 5/1876 |
| 9,693,715 B2 * | 7/2017 | Liu | H01L 27/1443 |
| 9,835,591 B2 * | 12/2017 | Dell | G01N 21/7746 |
| 2002/0076154 A1 | 6/2002 | Maisenhoelder et al. | |
| 2003/0003738 A1 | 1/2003 | Delwala | |
| 2003/0032039 A1 * | 2/2003 | Cunningham | B01L 3/5085 435/6.19 |
| 2003/0108291 A1 | 6/2003 | Duveneck et al. | |
| 2003/0232445 A1 | 12/2003 | Fulghum, Jr. | |
| 2004/0195511 A1 | 10/2004 | Elmore et al. | |
| 2004/0246490 A1 | 12/2004 | Wang | |
| 2005/0141843 A1 | 6/2005 | Warden et al. | |
| 2009/0075391 A1 | 3/2009 | Fulghum, Jr. | |
| 2010/0014802 A1 | 1/2010 | Chapman et al. | |
| 2010/0265504 A1 * | 10/2010 | Kopp | G02B 6/34 356/364 |
| 2010/0322555 A1 * | 12/2010 | Vermeulen | G02B 6/34 385/28 |
| 2011/0051772 A1 | 3/2011 | Fukuda | |
| 2011/0085238 A1 * | 4/2011 | Minemura | H01Q 9/0407 359/489.01 |
| 2011/0090931 A1 | 4/2011 | Murata | |
| 2012/0205524 A1 | 8/2012 | Mack et al. | |
| 2012/0308176 A1 | 12/2012 | McGinnis | |
| 2012/0315044 A1 | 12/2012 | McGreer et al. | |
| 2014/0085634 A1 | 3/2014 | Preston et al. | |
| 2014/0193115 A1 | 7/2014 | Popovic | |
| 2014/0193839 A1 | 7/2014 | Cunningham | |
| 2014/0268332 A1 | 9/2014 | Guo et al. | |
| 2014/0270618 A1 * | 9/2014 | Dinu | G02F 1/225 385/3 |
| 2015/0063753 A1 | 3/2015 | Evans et al. | |
| 2015/0098082 A1 | 4/2015 | Wang | |
| 2015/0110440 A1 | 4/2015 | Bodan et al. | |
| 2015/0131942 A1 | 5/2015 | Xu et al. | |
| 2015/0309263 A2 | 10/2015 | Abovitz et al. | |
| 2016/0161331 A1 | 6/2016 | Liu et al. | |
| 2016/0178516 A1 | 6/2016 | Abdulhalim | |
| 2016/0306115 A1 | 10/2016 | Koonen | |
| 2017/0168236 A1 * | 6/2017 | Huang | G02B 6/2773 |
| 2017/0179680 A1 * | 6/2017 | Mahgerefteh | H01S 5/3013 |
| 2018/0164214 A1 | 6/2018 | Rottenberg | |

FOREIGN PATENT DOCUMENTS

| | | |
|---|---|---|
| EP | 0818695 A2 | 1/1998 |
| JP | 2003-255116 A | 9/2003 |
| JP | 2004-054197 A | 2/2004 |
| WO | 2010/030251 A2 | 3/2010 |
| WO | 2010/030251 A3 | 3/2010 |

OTHER PUBLICATIONS

Marc Dandin, et al., "Optical filtering technologies for integrated fluorescence sensors", Lab on a Chip, vol. 7, Jul. 10, 2007, XP055095512, pp. 955-977.
Kalyani Chaganti, et al., "A simple miniature optical spectrometer with a planar waveguide grating coupler in combination with a (56) References Cited

OTHER PUBLICATIONS plano-convex lens", Optics Express, vol. 14, No. 9, May 1, 2006, XP0055001984, pp. 4064-4072.
Communication dated Jun. 28, 2016, issued by the European Patent Office in counterpart European Application No. 16155290.6.
B.E.A. Saleh et al.; "Fundamentals of Photonics"; Wiley Series in Pure and Applied Optics; Second Edition; 2009; 5 pages total.

\* cited by examiner

DUAL COUPLER DEVICE, SPECTROMETER INCLUDING THE DUAL COUPLER DEVICE, AND NON-INVASIVE BIOMETRIC SENSOR INCLUDING THE SPECTROMETER

CROSS-REFERENCE TO RELATED APPLICATION

This application is a continuation of U.S. patent application Ser. No. 15/045,895, filed on Feb. 17, 2016 in the U.S. Patent and Trademark Office, and claims priority from Korean Patent Application No. 10-2015-0024020, filed on Feb. 17, 2015 in the Korean Intellectual Property Office, the disclosures of which are incorporated herein by reference in their entireties.

BACKGROUND

1. Field

Apparatuses and methods consistent with exemplary embodiments relate to dual coupler devices configured to receive lights of different polarization components, spectrometers including the dual coupler devices, and non-invasive biometric sensors including the spectrometers.

2. Description of the Related Art

A non-invasive blood sugar measurement may be performed through spectroscopic analysis of a biometric signal that is obtained when incident light is reflected off the skin of a human subject. With improvements in performance of mobile apparatuses such as mobile phones, integrating a non-invasive biometric sensor into a mobile apparatus may be attempted. To this end, a micro spectrometer may be installed in a mobile apparatus.

For example, the micro spectrometer may be implemented as a linear variable filter (LVF)-based spectrometer or a filter array-based spectrometer. The LVF-based spectrometer may have a structure in which a spacer having a gradually changing thickness is disposed on a plurality of photodiode pixels so that the thickness of the LVF-based spectrometer varies continuously or in steps. Respective photodiode pixels in the LVF-based spectrometer may sense lights of different wavelength bands because a transmission wavelength varies depending on the thickness of the spacer. The filter array-based spectrometer may have a structure in which band-pass filters (BPFs) of different transmission bands are disposed in respective photodiode pixels.

SUMMARY

One or more exemplary embodiments provide dual coupler devices that are used in silicon photonics-based spectrometers and are configured to receive lights of different polarization components.

Further, one or more exemplary embodiments provide spectrometers including the dual coupler devices.

Further still, one or more exemplary embodiments provide non-invasive biometric sensors including the spectrometers.

According to an aspect of an exemplary embodiment, there is provided a dual coupler device including: a first coupler layer configured to receive a light of a first polarization component among incident lights; and a second coupler layer configured to receive a light of a second polarization component among the incident lights, wherein a polarization direction of the light of the first polarization component is perpendicular to a polarization direction of the light of the second polarization component, and the first coupler layer and the second coupler layer are spaced apart from each other and extended along a direction in which the incident lights propagate in the first coupler layer and the second coupler layer.

The first coupler layer and the second coupler layer may be parallel to each other.

Also, the first coupler layer and the second coupler layer may be disposed to face each other.

The dual coupler device may further include a transparent dielectric layer in which the first coupler layer and the second coupler layer may be buried.

The first coupler layer and the second coupler layer may have a higher refractive index than the transparent dielectric layer.

The first coupler layer and the second coupler layer may each include a grating-type coupler having a periodic grating structure.

The periodic grating structure of the first coupler layer may be configured to have selectivity with respect to the light of the first polarization component, and the periodic grating structure of the second coupler layer may be configured to have selectivity with respect to the light of the second polarization component.

The periodic grating structure of the first coupler layer may be configured to have selectivity with respect to a light of a first wavelength band, and the periodic grating structure of the second coupler layer may be configured to have selectivity with respect to a light of a second wavelength band that overlaps at least partially with the first wavelength band.

Herein, the first wavelength band and the second wavelength band may be substantially identical to each other.

The dual coupler device may further include a reflector configured to reflect light, which passes through the first coupler layer and the second coupler layer among the incident lights, towards the first coupler layer and the second coupler layer.

The reflector may be disposed apart from the first coupler layer by a first distance that creates destructive interference with the light of the second polarization component and constructive interference with the light of the first polarization component in the first coupler layer.

The reflector may be disposed apart from the second coupler layer by a second distance that creates destructive interference with the light of the first polarization component and constructive interference with the light of the second polarization component in the second coupler layer.

According to an aspect of another exemplary embodiment, there is provided a spectrometer including: a first coupler layer configured to receive a light of a first polarization component among incident lights; a second coupler layer configured to receive a light of a second polarization component among the incident lights; and a photodetector configured to detect the light received by each of the first coupler layer and the second coupler layer, wherein a polarization direction of the light of the first polarization component is perpendicular to a polarization direction of the light of the second polarization component, and the first coupler layer and the second coupler layer are spaced apart from each other and extended along a direction in which the incident lights propagate in the first coupler layer and the second coupler layer.

Herein, the first coupler layer may include: a first input coupler configured to selectively couple the light of the first polarization component; a first waveguide along which the light of the first polarization component coupled by the first input coupler propagates; a first resonator configured to resonate the light of the first polarization component coupled by the first input coupler; and a first output coupler configured to output the light of the first polarization component resonated by the first resonator to the photodetector.

Also, the second coupler layer may include: a second input coupler configured to selectively couple the light of the second polarization component; a second waveguide along which the light of the second polarization component coupled by the second input coupler propagates; a second resonator configured to resonate the light of the second polarization component coupled by the second input coupler; and a second output coupler configured to output the light of the second polarization component resonated by the second resonator to the photodetector.

The first coupler layer may include at least two first resonators configured to resonate lights of different wavelengths respectively, and the second coupler layer may include at least two second resonators configured to resonate lights of different wavelengths respectively.

One of the at least two first resonators of the first coupler layer and one of the at least two second resonators of the second coupler layer may be configured to resonate lights of substantially the same wavelength.

The first resonator of the first coupler layer and the second resonator of the second coupler layer configured to resonate lights of the same wavelength may be disposed to face each other.

The first coupler layer may include at least two first input couplers configured to selectively couple lights of different wavelengths respectively, and the second coupler layer may include at least two second input couplers configured to selectively couple lights of different wavelengths respectively.

The first input coupler may be optically connected to the at least two first resonators, and the second input coupler may be optically connected to the at least two second resonators.

The first coupler layer may include at least two first waveguides optically connected to the at least two first resonators respectively, and the second coupler layer may include at least two second waveguides optically connected to the at least two second resonators respectively.

The first output coupler and the second output coupler may be disposed respectively at positions that do not overlap with each other in a light propagation direction in the first waveguide and the second waveguide.

The spectrometer may further include a first reflector disposed to face the first input coupler and the second input coupler and configured to reflect light, which passes through the first coupler layer and the second coupler layer among the incident lights, towards the first coupler layer and the second coupler layer.

The first reflector may be disposed apart from the first coupler layer by a first distance that creates destructive interference with the light of the second polarization component and constructive interference with the light of the first polarization component in the first input coupler.

Also, the first reflector is disposed apart from the second coupler layer by a second distance that creates destructive interference with the light of the first polarization component and constructive interference with the light of the second polarization component in the second input coupler.

Also, the spectrometer may further include a second reflector disposed to face the first output coupler and the second output coupler and configured to reflect the light, which is output from the first output coupler and the second output coupler, to the photodetector.

According to an aspect of another exemplary embodiment, there is provided a non-invasive biometric sensor including: a light source configured to radiate an excitation light to an object; and a spectrometer configured to measure a spectrum distribution of a scattered light generated from the object by the excitation light. The spectrometer may include a first coupler layer configured to receive a light of a first polarization component among incident lights; a second coupler layer configured to receive a light of a second polarization component among the incident lights; and a photodetector configured to detect the light received by each of the first coupler layer and the second coupler layer, wherein a polarization direction of the light of the first polarization component is perpendicular to a polarization direction of the light of the second polarization component, and the first coupler layer and the second coupler layer are spaced apart from each other and extended along a direction in which the incident lights propagate in the first coupler layer and the second coupler layer.

According to an aspect of another exemplary embodiment, there is provided a spectrometer including: a first coupler layer configured to receive light of a p-polarization component through a first input coupler; a second coupler layer that is configured to receive light of a s-polarization component through a second input coupler and disposed to be apart from the first coupler layer in a first direction perpendicular to a second direction in which the light of the p-polarization component and the light of the s-polarization component propagate in the first coupler layer and the second coupler layer, respectively; and a reflector that is disposed to be apart from the first coupler layer and the second coupler layer in the first direction, aligned with the first input coupler and the second input coupler in the second direction, and configured to bounce off light incident from the first coupler input and the second input coupler back to the first input coupler and the second input coupler.

The first coupler layer may propagate the light of the p-polarization component towards a first output coupler disposed on the first coupler layer, the second coupler layer may propagate the light of the s-polarization component towards a second output coupler disposed on the second coupler layer, and the first output coupler may be disposed out of alignment with the second output coupler in the second direction.

The spectrometer of may further include another reflector that is disposed to be apart from the first coupler layer and the second coupler layer in the first direction and is aligned to bounce off light incident from the first output coupler and the second output coupler back to the first output coupler and the second output coupler.

BRIEF DESCRIPTION OF THE DRAWINGS

The above and/or other aspects will be more apparent by describing certain exemplary embodiments, with reference to the accompanying drawings, in which.

DETAILED DESCRIPTION

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

As used herein, the term "and/or" includes any and all combinations of one or more of the associated listed items. Expressions such as "at least one of," when preceding a list of elements, modify the entire list of elements and do not modify the individual elements of the list.

Hereinafter, dual coupler devices, spectrometers including the dual coupler devices, and non-invasive biometric sensors including the spectrometers according to exemplary embodiments will be described in detail with reference to the accompanying drawings. In the drawings, the sizes of elements may be exaggerated for clarity and convenience of description. It will be understood that when a layer is referred to as being "on" another layer, it may be directly on the other layer, or one or more intervening layers may also be present.

Figure 1:
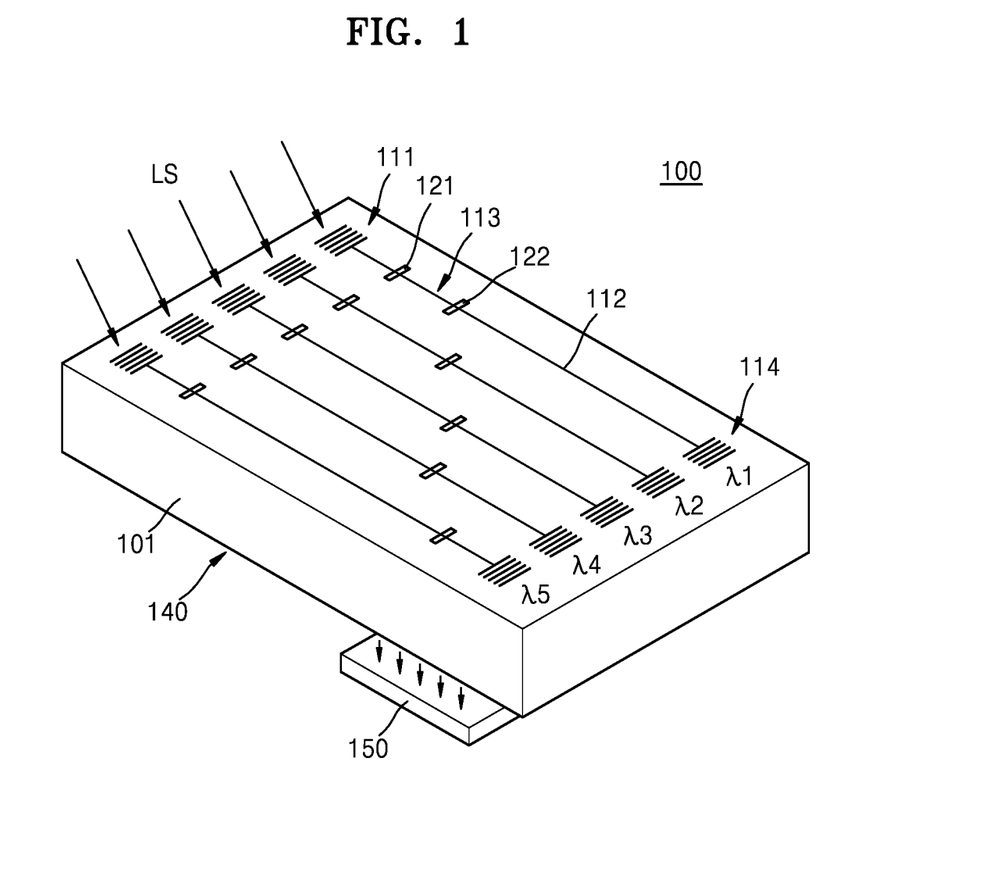
FIG. 1 is a schematic perspective view of a spectrometer according to an exemplary embodiment.

FIG. 1 is a schematic perspective view of a spectrometer according to an exemplary embodiment. Referring to FIG. 1, the spectrometer 100 may include a coupler device 140 based on silicon photonics and a photodetector 150. For example, the coupler device 140 may receive a scattered light LS from an object, divide the scattered light LS according to wavelengths, and provide the divided lights to the photodetector 150. The photodetector 150 may detect the intensities of a plurality of light beams divided by the coupler device 140 according to wavelengths. For example, the photodetector 150 may include a charge coupled device (CCD) image sensor, a complementary metal oxide semiconductor (CMOS) image sensor, or an array of photosensors. The spectrometer 100 may analyze a spectrum distribution of the scattered light LS in relevant wavelength bands.

The coupler device 140 may include an input coupler 111 configured to couple an incident light to the coupler device 140, a waveguide 112 along which the light coupled by the input coupler 111 propagates, a resonator 113 configured to resonate the light coupled by the input coupler 111, and an output coupler 114 configured to output the light resonated by the resonator 113 to the photodetector 150. The resonator 113 may include two resonator mirrors 121 and 122 disposed in the waveguide 112. In this structure, the light coupled by the input coupler 111 may propagate along the waveguide 112. Also, the light may resonate between the two resonator mirrors 121 and 122 of the resonator 113, and only the light having a resonance wavelength of the resonator 113 may be output from the resonator 113. The light output from the resonator 113 may propagate from the coupler device 140 to the photodetector 150 through the output coupler 114.

In order to divide the incident light according to wavelengths, the coupler device 140 may include at least two input couplers 111, at least two waveguides 112, at least two resonators 113, and at least two output couplers 114. The input couplers 111 may be configured to respectively couple lights of different wavelengths. For example, one of the input couplers 111 may be configured to selectively couple a light of a first wavelength band $\lambda 1$, and another of the input couplers 111 may be configured to selectively couple a light of a second wavelength band $\lambda 2$. Also, the resonators 113 may be configured to respectively resonate lights of different wavelengths. For example, one of the resonators 113 may be configured to resonate a light of the first wavelength band $\lambda 1$, and another of the resonators 113 may be configured to resonate a light of the second wavelength band $\lambda 2$. The resonance wavelength of the resonator 113 may be adjusted by the distance between the two resonator mirrors 121 and 122. The resonator 113 may be optically connected to any one of the input couplers 111 and resonate the light of substantially the same wavelength band as the selective wavelength band of the input coupler 111 connected thereto. For example, the input coupler 111 configured to selectively couple the light of the first wavelength band $\lambda 1$ may be optically connected to the resonator 113 having a resonance wavelength of the first wavelength band $\lambda 1$.

As illustrated in FIG. 1, the input couplers 111, the waveguides 112, the resonators 113, and the output couplers 114 may be disposed in parallel to each other at different positions in the widthwise direction of the coupler device 140. According to the present exemplary embodiment, the lights of different wavelengths may be incident on the photodetector 150 respectively from the output couplers 114 disposed at the different positions in the widthwise direction of the coupler device 140. Then, the lights of different wavelengths may be respectively incident on different positions of the photodetector 150. Thus, a spectrum distribution of the incident light may be analyzed by measuring the intensities of lights respectively incident on the different positions of the photodetector 150.

FIG. 1 exemplarily illustrates five input couplers 111, five waveguides 112, five resonators 113, and five output couplers 114. Thus, the spectrometer 100 may divide the incident light into five wavelength bands $\lambda 1, \lambda 2, \lambda 3, \lambda 4,$ and $\lambda 5$. However, the number of input couplers 111, waveguides 112, resonators 113, or output couplers 114 illustrated in FIG. 1 is merely exemplary. For example, ten or more input couplers 111, waveguides 112, resonators 113, and output couplers 114 may be disposed to analyze desired biometric information on the basis of biometric optical signals transmitted or scattered from a living body.

Also, although FIG. 1 illustrates that the input coupler 111, the resonator 113, and the output coupler 114 are physically connected through one waveguide 112, this is merely exemplary. That is, the input coupler 111, the resonator 113, and the output coupler 114 may not be physically connected through one waveguide 112, and any means may be used to transmit the light from the input coupler 111 to the resonator 113 and transmit the light from the resonator 113 to the output coupler 114. For example, an empty space may exist between the resonator 113 and the output coupler 114, and the waveguide 112 may exist only partially therein.

Thus, the input coupler 111, the waveguide 112, the resonator 113, and the output coupler 114 may be optically connected although not physically connected. Also, a light path from the input coupler 111 to the output coupler 114 may not necessarily be a straight line.

Figure 2:
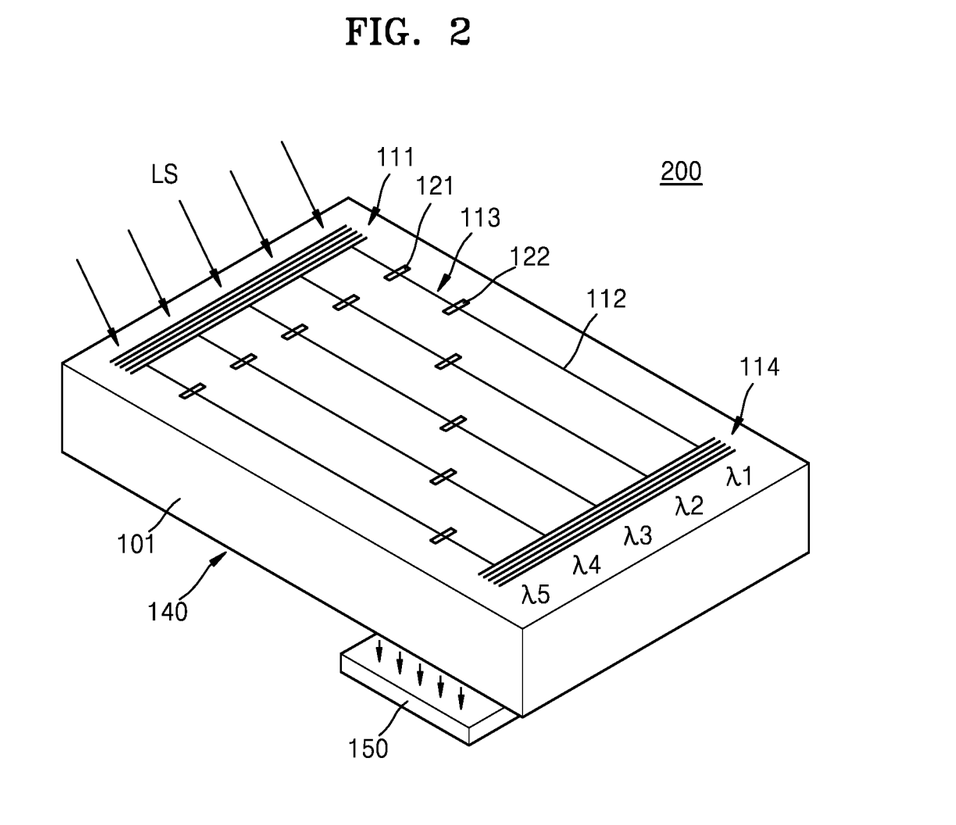
FIG. 2 is a schematic perspective view of a spectrometer according to another exemplary embodiment.

FIG. 2 is a schematic perspective view of a spectrometer according to another exemplary embodiment. The spectrometer 200 illustrated in FIG. 2 may include a single input coupler 111 and a single output coupler 114. The input coupler 111 and output coupler 114 may be optically connected to at least two waveguides 112 and at least two resonators 113. Other than the number of the input coupler 111 and the output coupler 114, the configuration of the spectrometer 200 illustrated in FIG. 2 may be identical to the configuration of the spectrometer 100 illustrated in FIG. 1. In the exemplary embodiment illustrated in FIG. 2, the input coupler 111 and the output coupler 114 may not have a wavelength selectivity. For example, the input coupler 111 may couple lights of all wavelength bands and provide the coupled lights to waveguides 112 respectively. Also, the resonators 113 having different resonance wavelengths respectively may output only the lights of the respective wavelengths to the output coupler 114.

Also, although FIG. 2 illustrates that the spectrometer 200 includes one input coupler 111 and one output coupler 114, at least two input couplers 111 having a wavelength selectivity and one output coupler 114 not having a wavelength selectivity may be included according to another exemplary embodiment. Also, one input coupler 111 not having a wavelength selectivity and at least two output couplers 114 having a wavelength selectivity may be included according to another exemplary embodiment.

In general, the input coupler 111 includes a grating-type coupler having a periodic grating structure, and the grating-type coupler has a polarization selectivity. For example, the input coupler 111 may couple either a p-polarization component (also referred to as transverse-magnetic (TM) component) or an s-polarization component (also referred to as transverse-electric (TE) component) of light incident onto the input coupler 111. When some polarization components of the incident light are not coupled, the coupling efficiency of the input coupler 11 may degrade and light loss may occur. In that case, stable spectrum analysis of the spectrometer may be difficult. The coupler device 140 according to the present exemplary embodiment may be configured to have a two-layer structure having a selectivity with respect to the p-polarization component and the s-polarization component to improve the coupling efficiency by coupling the lights of all polarization components.

Figure 3:
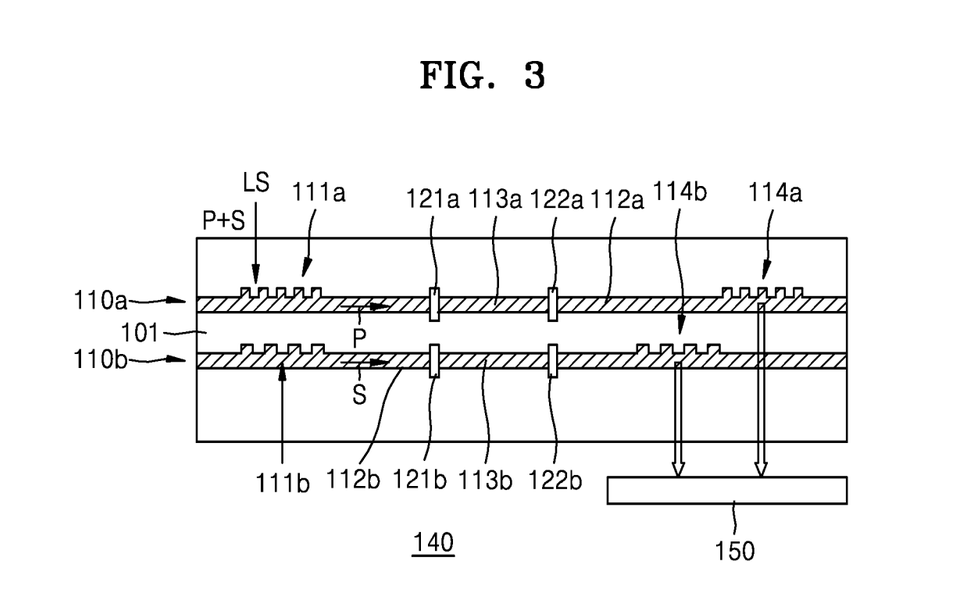
FIG. 3 is a schematic cross-sectional view of a coupler device according to an exemplary embodiment.

For example, FIG. 3 is a schematic cross-sectional view of a coupler device according to an exemplary embodiment. Referring to FIG. 3, the coupler device 140 may include a first coupler layer 110a and a second coupler layer 110b. Also, the coupler device 140 may further include a transparent dielectric layer 101 in which the first coupler layer 110a and the second coupler layer 110b are buried. The first coupler layer 110a and the second coupler layer 110b may be fixed and disposed respectively in different layers by the transparent dielectric layer 101. Herein, the first coupler layer 110a and the second coupler layer 110b may include a material having a higher refractive index than the transparent dielectric layer 101 therearound. For example, the transparent dielectric layer 101 may include $SiO_2$ or siloxane-based spin-on glass (SOG), and the first coupler layer 110a and the second coupler layer 110b may include a high-refractive index material such as $TiO_2$, $SiN_3$, ZnS, ZnSe, or $Si_3N_4$. Also, the first coupler layer 110a and the second coupler layer 110b may include the same material or may include different materials to improve the wavelength selectivity.

As illustrated in FIG. 3, the first coupler layer 110a and the second coupler layer 110b may be disposed respectively in different layers along an incident light propagation direction in the transparent dielectric layer 101. The first coupler layer 110a and the second coupler layer 110b may have opposite polarization selectivities. For example, the first coupler layer 110a may be configured to have a selectivity with respect to the light of the p-polarization component, and the second coupler layer 110b may be configured to have a selectivity with respect to the light of the s-polarization component. In this regard, the coupler device 140 may be a dual coupler device having a dual-layer structure.

The first coupler layer 110a may include a first input coupler 111a, a first waveguide 112a, a first resonator 113a, and a first output coupler 114a that are disposed in the same layer. Although not illustrated in FIG. 3, as illustrated in FIGS. 1 and 2, the first coupler layer 110a may include at least two first input couplers 111a, at least two first waveguides 112a, at least two first resonators 113a, and at least two first output couplers 114a, which have different wavelength selectivities. Also, each of the first resonators 113a may include two resonator mirrors 121a and 122a that are disposed in the first waveguide 112a. Herein, the first input coupler 111a may be, for example, a grating-type coupler having a periodic grating structure configured to have a selectivity with respect to the light of the p-polarization component. Thus, the light of the p-polarization component among the incident lights may be provided to the first waveguide 112a through the first input coupler 111a.

Also, the second coupler layer 110b may include a second input coupler 111b, a second waveguide 112b, a second resonator 113b, and a second output coupler 114b that are disposed in the same layer. Like the first coupler layer 110a, the second coupler layer 110b may include at least two second input couplers 111b, at least two second waveguides 112b, at least two second resonators 113b, and at least two second output couplers 114b, which have different wavelength selectivities. Each of the second resonators 113b may include two resonator mirrors 121b and 122b that are disposed in the second waveguide 112b. The second input coupler 111b may be, for example, a grating-type coupler having a periodic grating structure configured to have a selectivity with respect to the light of the s-polarization component. Thus, the light of the s-polarization component among the incident lights may be provided to the second waveguide 112b through the second input coupler 111b.

The first coupler layer 110a and the second coupler layer 110b may be disposed in different layers to be parallel to and face each other. For example, the first input coupler 111a, the first waveguide 112a, the first resonator 113a, and the first output coupler 114a of the first coupler layer 110a may be arranged in parallel to the second input coupler 111b, the second waveguide 112b, the second resonator 113b, and the second output coupler 114b of the second coupler layer 110b. Also, the at least two first input couplers 111a, the at least two first waveguides 112a, and the at least two first resonators 113a of the first coupler layer 110a arranged in the widthwise direction of the coupler device 140 may be disposed to face the at least two second input couplers 111b, the at least two second waveguides 112b, and the at least two second resonators 113b of the second coupler layer 110b, respectively. When two elements face each other, the two elements appear to overlap with each other when viewed in a height wise direction, that is, the vertical direction of the top surface of the transparent dielectric layer 101.

The first and second input couplers 111a and 111b disposed to face each other may be configured to have different polarization selectivities with respect to the same wavelength band. For example, the first input coupler 111a configured to selectively couple the light of the first wavelength band λ1 having the p-polarization component may be disposed to face the second input coupler 111b configured to selectively couple the light of the first wavelength band λ1 having the s-polarization component. However, the wavelength bands of the lights coupled respectively by the first input coupler 111a and the second input coupler 111b facing each other may not necessarily be identical to each other. Instead, the wavelength band of the light coupled by the first input coupler 111a may overlap partially with the wavelength band of the light coupled by the second input coupler 111b facing the first input coupler 111a. For example, the wavelength band of the light coupled by the first input coupler 111a may be λ1±Δλ, and the wavelength band of the light coupled by the second input coupler 111b facing the first input coupler 111a may be λ1±Δλ'.

Likewise, the first and second resonators 113a and 113b disposed to face each other may be configured to have substantially the same resonance wavelength. For example, the first resonator 113a configured to resonate the light of the first wavelength band λ1 may be disposed to face the second resonator 113b configured to resonate the light of the first wavelength band λ1. The distance between the two resonator mirrors 121a and 122a and the distance between the two resonator mirrors 121b and 122b in the first and second resonators 113a and 113b disposed to face each other may be equal to each other.

As illustrated in FIG. 3, the first and second output couplers 114a and 114b may be disposed respectively at positions that do not overlap with each other in a lengthwise direction, that is, the light propagation direction in the first and second waveguides 112a and 112b. This is done so that the light output from the first output coupler 114a and propagating toward the photodetector 150 may not pass through the second output coupler 114b. Thus, the light propagating from the first output coupler 114a toward the photodetector 150 may reach the photodetector 150 without being obstructed by the second output coupler 114b.

Although it has been described above that at least two first input couplers 111a, at least two second input couplers 111b, at least two first output couplers 114a, and at least two second output couplers 114b are disposed, the coupler device 140 illustrated in FIG. 3 may be applied to the spectrometer 100 illustrated in FIG. 1 and also to the spectrometer 200 illustrated in FIG. 2. For example, only one first input coupler 111a may be optically connected to the at least two first waveguides 112a and the at least two first resonators 113a. Also, only one second input coupler 111b may be optically connected to the at least two second waveguides 112b and the at least two second resonators 113b.

The coupling efficiency of the coupler device 140 may be improved by using the first coupler layer 110a and the second coupler layer 110b operating independently of each other as described above. For example, the first coupler layer 110a may be designed to optimize the reception of the light of the p-polarization component, and the second coupler layer 110b may be designed to optimize the reception of the light of the s-polarization component. Thus, the coupler device 140 may receive both the light of the p-polarization component and the light of the s-polarization component, which are included in the incident lights, with high efficiency. Consequently, the spectrum analysis accuracy of the spectrometers 100 and 200 including the coupler device 140 may be improved. Also, the first coupler layer 110a and the second coupler layer 110b may be arranged in different-height layers without increasing the area of the coupler device 140. Thus, the spectrometers 100 and 200 including the coupler device 140 may be miniaturized.

Figure 4:
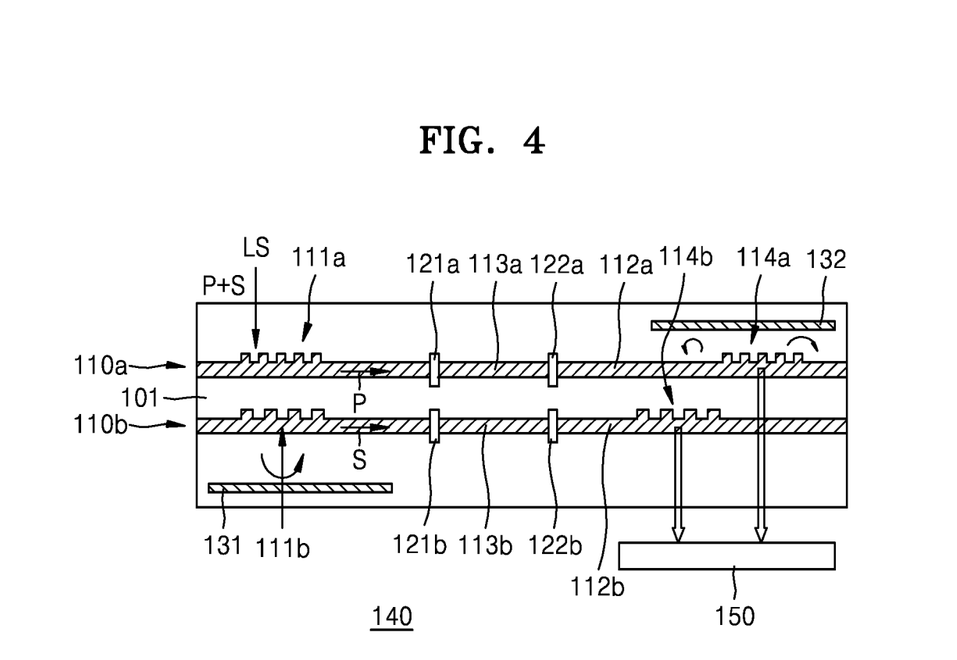
FIG. 4 is a schematic cross-sectional view of a coupler device according to another exemplary embodiment.

FIG. 4 is a schematic cross-sectional view of a coupler device according to another exemplary embodiment. As shown in FIG. 4, the coupler device 140 may further include a first reflector 131 and a second reflector 132. The first reflector 131 may be disposed to face the first and second input couplers 111a and 111b, and the second reflector 132 may be disposed to face the first and second output couplers 114a and 114b.

The first reflector 131 is configured to reflect light, which passes through the first and second input couplers 111a and 111b without being absorbed by the first and second input couplers 111a and 111b, to the first and second input couplers 111a and 111b. When light is projected onto the first and second input couplers 111a and 111b, some of the light passes through the first and second input couplers 111a and 111b without being absorbed and reaches the first reflector 131. The light incident on the first reflector 131 may bounce back in the direction it comes from. The first and second input couplers 111a and 111b may receive the light bouncing off the first reflector 131. Thus, the coupling efficiency of the coupler device 140 may be further improved by reusing the light that remains without being absorbed. The first reflector 131 may be disposed on an opposite side to a light incident surface of the coupler device 140 on which the light is incident. For example, when the light is incident on the top surface of the coupler device 140, the first reflector 131 may be disposed between the bottom surface of the coupler device 140 and the second input coupler 111b.

In particular, the coupling efficiency of the first and second input couplers 111a and 111b may be further improved by using the fact that a phase difference occurs between the reflected light of the p-polarization component and the reflected light of the s-polarization component when the light is incident on the first reflector 131 at an angle smaller than the Brewster's angle. In general, when the first reflector 131 is a perfect conductor, the phase difference between the reflected light of the p-polarization component and the reflected light of the s-polarization component is 180°, and the same effect may be achieved also in a dielectric Bragg reflector. Thus, the distance between the first input coupler 111a and the first reflector 131 may be set to cause a destructive interference between the incident light and the reflected light with respect to the light of the s-polarization component and a constructive interference between the incident light and the reflected light with respect to the light of the p-polarization component in the first input coupler 111a. Then, the selectivity of the light of the p-polarization component in the first input coupler 111a may be further improved. Also, the distance between the second input coupler 111b and the first reflector 131 may be set to cause a destructive interference between the incident light and the reflected light with respect to the light of the p-polarization component and a constructive interference between the incident light and the reflected light with respect to the light of the s-polarization component in the second input coupler 111b. Then, the selectivity of the light of the s-polarization component in the second input coupler 111b may be further improved.

For example, a finite-difference in time-domain (FDTD) simulation is performed to verify the effect of the spectrometer 100 illustrated in FIG. 1. In the FDTD simulation, it is assumed that a grating pitch size of the input coupler 111 is 600~700 nm, the waveguide 112 is formed of $Si_3N_4$, the transparent dielectric layer 101 is formed of $SiO_2$, a distance between the first coupler layer 110*a* and the second coupler layer 110*b* is 2.2 um, and a distance between the second coupler layer 110*b* and the first reflector 131 is 540 nm. As a result of the FDTD simulation, when the first reflector 131 is not disposed, about 25% of the light of the p-polarization component is absorbed by the first input coupler 111*a* and about 6% of the light of the p-polarization component is absorbed by the second input coupler 111*b*. Also, about 4% of the light of the s-polarization component is absorbed by the first input coupler 111*a* and about 11% of the light of the s-polarization component is absorbed by the second input coupler 111*b*. On the other hand, when the first reflector 131 is disposed, about 60% of the light of the p-polarization component is absorbed by the first input coupler 111*a* and about 1% of the light of the p-polarization component is absorbed by the second input coupler 111*b*. Also, about 2% of the light of the s-polarization component is absorbed by the first input coupler 111*a* and about 50% of the light of the s-polarization component is absorbed by the second input coupler 111*b*. Thus, the signal-to-noise ratio and the coupling efficiency of the coupler device 140 may be greatly improved.

Also, the second reflector 132 is configured to reflect the light, which is scattered without propagating from the first and second output couplers 114*a* and 114*b*, to the photodetector 150. The output coupling efficiency may be improved by increasing the amount of light output to the photodetector 150 by using the second reflector 132. The second reflector 132 may be disposed on an opposite side to the photodetector 150. For example, when the photodetector 150 is disposed to face the bottom surface of the coupler device 140, the second reflector 132 may be disposed between the top surface of the coupler device 140 and the first input coupler 111*a*.

The spectrometers 100 and 200 may be manufactured to be micro-sized in the form of a semiconductor chip while having high resolution and accuracy. Thus, a non-invasive biometric sensor installed in a mobile apparatus may be implemented by using the above spectrometers 100 and 200.

Figure 5:
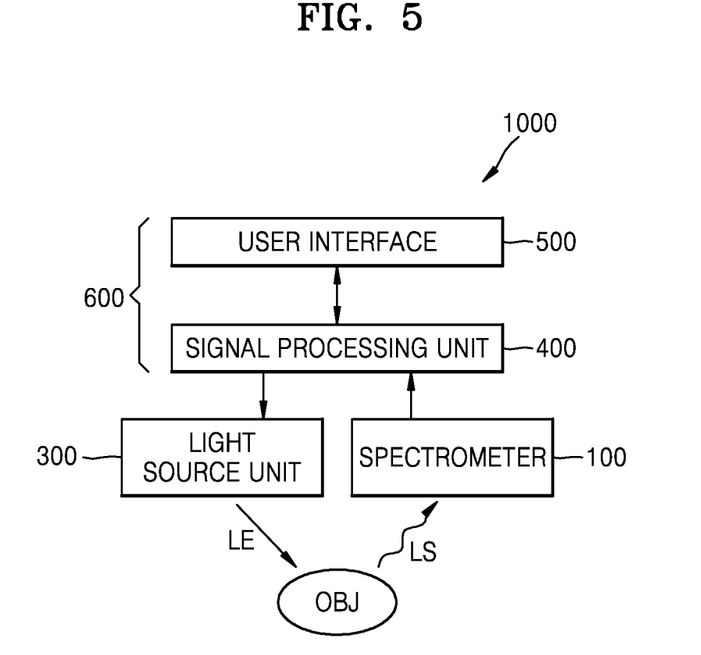
FIG. 5 is a schematic block diagram of a non-invasive biometric sensor according to an exemplary embodiment.

For example, FIG. 5 is a schematic block diagram of a non-invasive biometric sensor including the spectrometer of FIG. 1 according to an exemplary embodiment. Referring to FIG. 5, the non-invasive biometric sensor 1000 may include a light source unit (e.g., light emitter) 300 configured to radiate an excitation light LE to an object OBJ, and a spectrometer 100 configured to spectroscope a scattered light LS generated from the object OBJ. Herein, the object OBJ may include a human body, a living body of an animal, or a food. For example, the object OBJ may be a human body for blood sugar measurement or a food for freshness measurement, and may be a sample for analysis of air pollution or water pollution.

The light source unit 300 may include a light source and may also include at least one optical member for guiding the light from the light source to a desired position of the object OBJ. The light source may be configured to radiate a light of a wavelength band predetermined based on an analysis target property of the object OBJ. For example, the light source may radiate a near-infrared light of a wavelength band of about 0.8 μm to about 2.5 μm. The light source may include, for example, a light-emitting diode (LED) or a laser diode (LD).

Also, the non-invasive biometric sensor 1000 may further include a control unit (e.g., a controller or hardware computing device) 600 configured to analyze the properties of the object OBJ on the basis of signals sensed by the spectrometer 100 and generate corresponding control signals. The control unit 600 may include a user interface 500 and a signal processing unit (e.g., signal processor) 400. The user interface unit 500 may include an input unit and a display. The signal processing unit 400 may analyze the properties of the object OBJ on the basis of the signals sensed by the spectrometer 100. For example, the signal processing unit 400 may analyze the properties of the object OBJ by Raman spectroscopy or near-infrared (NIR) absorption spectrum analysis. The Raman spectroscopy may use scattering (particularly inelastic scattering) in which the light input into the object OBJ is scattered in various directions by colliding with molecules or atoms included in the object OBJ. In the inelastic scattering, instead of being simply reflected from the surface of molecules or atoms, the incident light is emitted after being absorbed into molecules or atoms, wherein the scattered light may have a longer wavelength than the incident light and a wavelength difference between the scattered light and the incident light may be about 200 nm or less. Various properties, such as the structure of molecules and the vibration of molecules in the object OBJ, may be detected by analyzing the spectrum of the scattered light.

The signal processing unit 400 may process the analysis result into a video signal to be displayed on the display of the user interface 500. Also, the signal processing unit 400 may transmit a control signal to the light source unit 300 according to the input from the user interface 500. For example, the signal processing unit 400 may be implemented by a microprocessor.

The spectrometer 100 and the control unit 600 may be connected to each other via wire or wireless communication. For example, the non-invasive biometric sensor 1000 may be implemented as a mini portable device in which the spectrometer 100 and the control unit 600 are connected by wire. As another example, the control unit 600 may be mounted on a portable mobile communication device to wirelessly communicate with the spectrometer 100.

Figure 6:
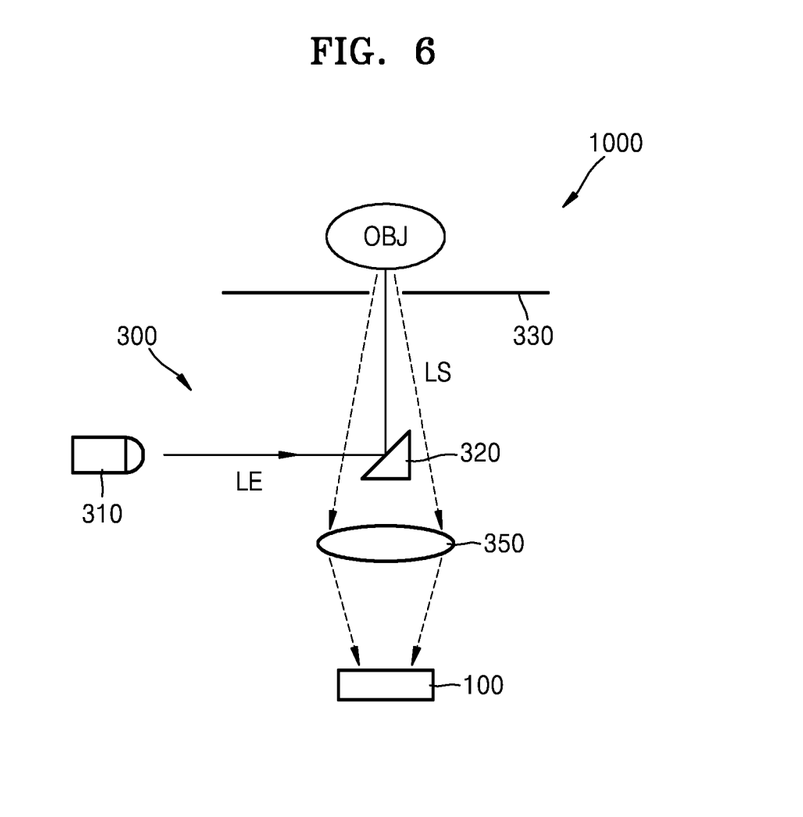
FIG. 6 illustrates an example of an optical arrangement of the non-invasive biometric sensor illustrated in FIG. 5.

FIG. 6 illustrates an example of an optical arrangement of the non-invasive biometric sensor 1000 illustrated in FIG. 5. Referring to FIG. 6, the non-invasive biometric sensor 1000 may be implemented as a reflection type. An optical system of the non-invasive biometric sensor 1000 may be configured such that the spectrometer 100 may sense the scattered light LS reflected from the object OBJ. For example, the light source unit 300 may include a light source 310, a light path converter 320, and a diaphragm 330. Although the light path converter 320 is illustrated as being a prism type, this is merely exemplary and the light path converter 320 may also be a beam splitter type or a flat mirror type. The light path converter 320 may be omitted according to the position of the light source 310. Also, the light source unit 300 may further include an optical lens 350 configured to focus the scattered light LS from the object OBJ on the spectrometer 100.

The excitation light LE radiated from the light source 310 collides with a molecular structure in the object OBJ. In turn, the excitation light is absorbed into the molecular structure and emitted therefrom so that a wavelength-converted scattered light LS is output from the object OBJ. The scattered light LS, that is, a biometric optical signal may include various spectrums having different wavelength conversion degrees according to the molecular states in the object OBJ. The non-invasive biometric sensor 1000 includes an optical system structure in which the scattered light LS output along the same path as the input path of the excitation light LE to the object OBJ is input to the spectrometer 100. Also, the non-invasive biometric sensor 1000 may further include an additional optical device that branches the scattered light LS to the spectrometer 100.

Figure 7:
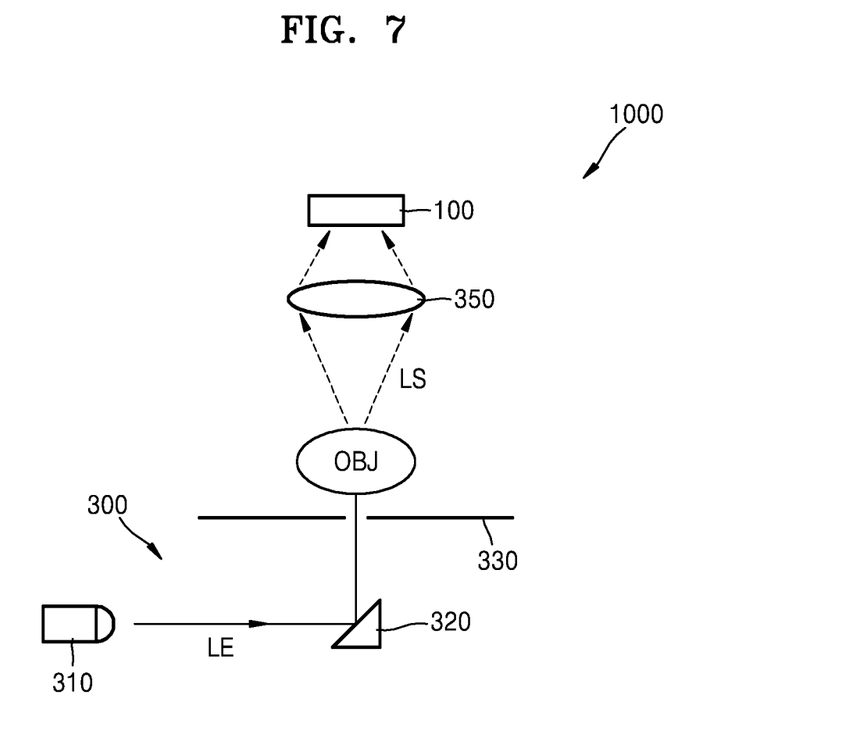
FIG. 7 illustrates another example of the optical arrangement of the non-invasive biometric sensor illustrated in FIG. 5.

FIG. 7 illustrates another example of the optical arrangement of the non-invasive biometric sensor 1000 illustrated in FIG. 5. Referring to FIG. 7, the non-invasive biometric sensor 1000 may be implemented as a transmission type. An optical system of the non-invasive biometric sensor 1000 may be configured such that the spectrometer 100 may sense the scattered light LS transmitted through the object OBJ. For example, the light source unit 300 may include a light source 310, a light path converter 320, and a diaphragm 330. Although the light path converter 320 is illustrated as being a prism type, this is merely exemplary and the light path converter 320 may also be a beam splitter type or a flat mirror type. The light path converter 320 may be omitted according to the position of the light source 310. The light source unit 300 may further include an optical lens 350 configured to focus the scattered light LS from the object OBJ on the spectrometer 100.

The excitation light LE radiated from the light source 310 collides with a molecular structure in the object OBJ. In turn, the excitation light LE is absorbed into the molecular structure and emitted therefrom so that a wavelength-converted scattered light LS is output from the object OBJ. The scattered light LS, that is, a biometric optical signal may include various spectrums having different wavelength conversion degrees according to the molecular states in the object OBJ. The non-invasive biometric sensor 1000 includes an optical system structure in which the scattered light LS output through the object OBJ is input to the spectrometer 100.

Figure 8:
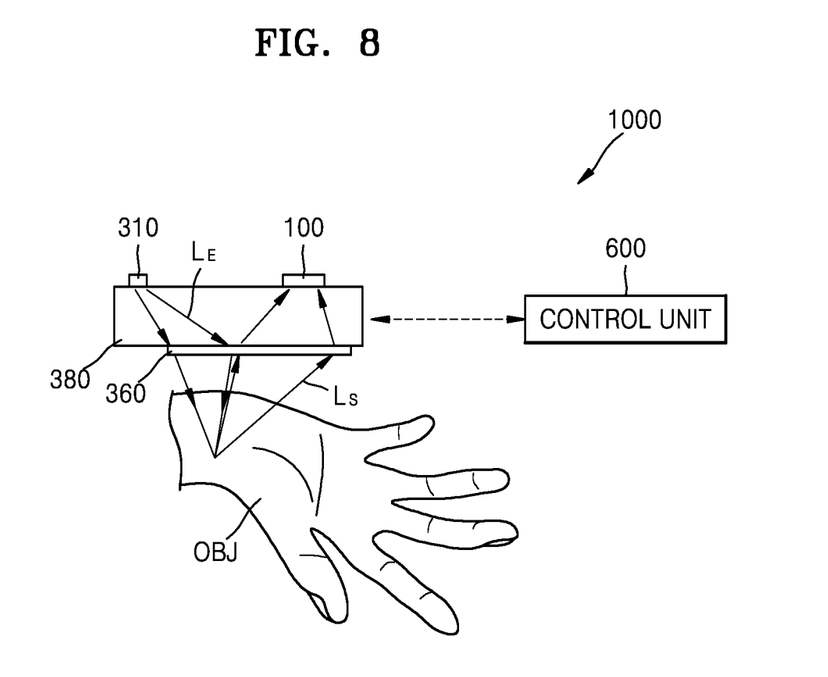
FIG. 8 illustrates another example of the optical arrangement of the non-invasive biometric sensor illustrated in FIG. 5.

FIG. 8 illustrates another example of the optical arrangement of the non-invasive biometric sensor 1000 illustrated in FIG. 5. Referring to FIG. 8, the non-invasive biometric sensor 1000 may further include a base 380, and the light source 310 and the spectrometer 100 may be disposed on the same surface of the base 380 or on different surfaces of the base 380. For example, the base 380 may be formed of a transparent material, and the light source 310 and the spectrometer 100 may be disposed on the same surface of the base 380 while being spaced apart from each other. In this case, the light source 310 may be disposed to radiate the excitation light LE to the object OBJ through the base 380. The spectrometer 100 may be disposed to sense the scattered light LS that is input from the object OBJ through the base 380. Also, on the other surface of the base 380, an optical lens 360 may be further disposed to focus the excitation light LE from the light source 310 on the object OBJ and focus the scattered light LS from the object OBJ on the spectrometer 100.

The base 380 may be formed of a flexible material. In this case, the non-invasive biometric sensor 1000 may be configured to be wearable on the object OBJ. For example, the non-invasive biometric sensor 1000 may be implemented as an armlet-type non-invasive blood sugar sensor. In this case, the control unit 600 may be disposed on the base 380 together with the spectrometer 100. As another example, the non-invasive biometric sensor 1000 may be implemented in such a manner that only the light source 310 and the spectrometer 100 are formed in an armlet-type wearable structure and the control unit 600 is mounted on a mobile device.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A dual coupler device comprising:
 a first coupler layer configured to receive light of a first polarization component among incident light, the first coupler layer comprising:
  a first waveguide along which the light of the first polarization component propagates;
  a first resonator disposed in the first waveguide, the first resonator being configured to resonate light of a first wavelength band among the light of the first polarization component;
  a second waveguide along which the light of the first polarization component propagates; and
  a second resonator disposed in the second waveguide, the second resonator being configured to resonate light of a second wavelength band different from the first wavelength band among the light of the first polarization component; and
 a second coupler layer configured to receive light of a second polarization component among the incident light, the second coupler layer comprising:
  a third waveguide along which the light of the second polarization component propagates;
  a third resonator disposed in the third waveguide, the third resonator being configured to resonate light of the first wavelength band among the light of the second polarization component;
  a fourth waveguide along which the light of the second polarization component propagates; and
  a fourth resonator disposed in the fourth waveguide, the fourth resonator being configured to resonate light of the second wavelength band among the light of the second polarization component.

2. The dual coupler device of claim 1, wherein the first coupler layer and the second coupler layer are spaced apart from each other in a vertical direction and extended along a horizontal direction in which the incident light propagates in the first coupler layer and the second coupler layer.

3. The dual coupler device of claim 1, further comprising a transparent dielectric layer in which the first coupler layer and the second coupler layer are buried,
 wherein the first coupler layer and the second coupler layer have a refractive index that is higher than a refractive index of the transparent dielectric layer.

4. The dual coupler device of claim 1, wherein the first waveguide and the third waveguide are parallel to and face each other, and
 wherein the second waveguide and the fourth waveguide are parallel to and face each other.

5. The dual coupler device of claim 1, wherein the first coupler layer further comprises:
 a first input coupler connected to the first waveguide and configured to couple the light of the first wavelength band among the light of the first polarization component to the first waveguide; and
 a second input coupler connected to the second waveguide and configured to couple the light of the second wavelength band among the light of the first polarization component to the first waveguide, and wherein the second coupler layer further comprises:
a third input coupler connected to the third waveguide and configured to couple the light of the first wavelength band among the light of the second polarization component to the third waveguide; and
a fourth input coupler connected to the fourth waveguide and configured to couple the light of the second wavelength band among the light of the second polarization component to the fourth waveguide.

6. The dual coupler device of claim 1, wherein the first coupler layer further comprises:
a first output coupler connected to the first waveguide and configured to output the light resonated by the first resonator; and
a second output coupler connected to the second waveguide and configured to output the light resonated by the second resonator, and wherein the second coupler layer further comprises:
a third output coupler connected to the third waveguide and configured to output the light resonated by the third resonator; and
a fourth output coupler connected to the fourth waveguide and configured to output the light resonated by the fourth resonator.

7. The dual coupler device of claim 1, wherein the first coupler layer further comprises a first input coupler connected to the first waveguide and the second waveguide, the first input coupler being configured to couple the light of the first polarization component to the first waveguide and the second waveguide, and wherein the second coupler layer further comprises a second input coupler connected to the third waveguide and the fourth waveguide, the second input coupler being configured to couple the light of the second polarization component to the third waveguide and the fourth waveguide.

8. The dual coupler device of claim 7, further comprising a reflector disposed to face the first input coupler and the second input coupler, the reflector being configured to reflect light, which passes through the first input coupler and the second input coupler layer, toward the first input coupler and the second input coupler layer.

9. The dual coupler device of claim 1, wherein the first coupler layer further comprises a first output coupler connected to the first waveguide and the second waveguide, the first output coupler being configured to output the light resonated by the first resonator and the light resonated by the second resonator, and wherein the second coupler layer further comprises a second output coupler connected to the third waveguide and the fourth waveguide, the second output coupler being configured to output the light resonated by the third resonator and the light resonated by the fourth resonator.

10. The dual coupler device of claim 9, further comprising a reflector disposed to face the first output coupler and the second output coupler, the reflector being configured to reflect light scattered from the first output coupler and the second output coupler layer.

11. A spectrometer comprising:
a first coupler layer configured to receive light of a first polarization component among incident light;
a second coupler layer configured to receive light of a second polarization component among the incident light; and
a photodetector configured to detect the light received by each of the first coupler layer and the second coupler layer, and wherein the first coupler layer comprises:
a first waveguide along which the light of the first polarization component propagates;
a first resonator disposed in the first waveguide, the first resonator being configured to resonate light of a first wavelength band among the light of the first polarization component;
a second waveguide along which the light of the first polarization component propagates; and
a second resonator disposed in the second waveguide, the second resonator being configured to resonate light of a second wavelength band different from the first wavelength band among the light of the first polarization component, and wherein the second coupler layer comprises;
a third waveguide along which the light of the second polarization component propagates;
a third resonator disposed in the third waveguide, the third resonator being configured to resonate light of the first wavelength band among the light of the second polarization component;
a fourth waveguide along which the light of the second polarization component propagates; and
a fourth resonator disposed in the fourth waveguide, the fourth resonator being configured to resonate light of the second wavelength band among the light of the second polarization component.

12. The spectrometer of claim 11, wherein the first coupler layer and the second coupler layer are spaced apart from each other in a vertical direction and extended along a horizontal direction in which the incident light propagates in the first coupler layer and the second coupler layer.

13. The spectrometer of claim 11, further comprising a transparent dielectric layer in which the first coupler layer and the second coupler layer are buried, wherein the first coupler layer and the second coupler layer have a refractive index that is higher than a refractive index of the transparent dielectric layer.

14. The spectrometer of claim 11, wherein the first waveguide and the third waveguide are parallel to and face each other, and wherein the second waveguide and the fourth waveguide are parallel to and face each other.

15. The spectrometer of claim 11, wherein the first coupler layer further comprises:
a first input coupler connected to the first waveguide and configured to couple the light of the first wavelength band among the light of the first polarization component to the first waveguide; and
a second input coupler connected to the second waveguide and configured to couple the light of the second wavelength band among the light of the first polarization component to the first waveguide, and wherein the second coupler layer further comprises:
a third input coupler connected to the third waveguide and configured to couple the light of the first wavelength band among the light of the second polarization component to the third waveguide; and
a fourth input coupler connected to the fourth waveguide and configured to couple the light of the second wavelength band among the light of the second polarization component to the fourth waveguide.

16. The spectrometer of claim 11, wherein the first coupler layer further comprises:

a first output coupler connected to the first waveguide and configured to output the light resonated by the first resonator to the photodetector; and a second output coupler connected to the second waveguide and configured to output the light resonated by the second resonator to the photodetector, and wherein the second coupler layer further comprises:

a third output coupler connected to the third waveguide and configured to output the light resonated by the third resonator to the photodetector; and a fourth output coupler connected to the fourth waveguide and configured to output the light resonated by the fourth resonator to the photodetector.

17. The spectrometer of claim 11, wherein the first coupler layer further comprises a first input coupler connected to the first waveguide and the second waveguide, the first input coupler being configured to couple the light of the first polarization component to the first waveguide and the second waveguide, and wherein the second coupler layer further comprises a second input coupler connected to the third waveguide and the fourth waveguide, the second input coupler being configured to couple the light of the second polarization component to the third waveguide and the fourth waveguide.

18. The spectrometer of claim 17, further comprising a reflector disposed to face the first input coupler and the second input coupler, the reflector being configured to reflect light, which passes through the first input coupler and the second input coupler layer, toward the first input coupler and the second input coupler layer.

19. The spectrometer of claim 11, wherein the first coupler layer further comprises a first output coupler connected to the first waveguide and the second waveguide, the first output coupler being configured to output the light resonated by the first resonator and the light resonated by the second resonator to the photodetector, and wherein the second coupler layer further comprises a second output coupler connected to the third waveguide and the fourth waveguide, the second output coupler being configured to output the light resonated by the third resonator and the light resonated by the fourth resonator to the photodetector.

20. The spectrometer of claim 19, further comprising a reflector disposed to face the first output coupler and the second output coupler, the reflector being configured to reflect, light scattered from the first output coupler and the second output coupler layer, toward the photodetector.

* * * * *